(12) United States Patent
Kralchevsky et al.

(10) Patent No.: US 11,318,080 B2
(45) Date of Patent: May 3, 2022

(54) CONDITIONING SHAMPOO COMPOSITION

(71) Applicant: KL-KEPONG OLEOMAS SDN BHD, Selangor Darul Ehsan (MY)

(72) Inventors: Peter Atanassov Kralchevsky, Sofia (BG); Rumyana Dobreva Stanimirova, Sofia (BG); Jordan Todorov Petkov, Stockport (GB); Hui Xu, Selangor (MY)

(73) Assignee: KL-KEPONG OLEOMAS SDN BHD, Selangor Darul Ehsan (MY)

( * ) Notice: Subject to any disclaimer, the term of this patent is extended or adjusted under 35 U.S.C. 154(b) by 0 days.

(21) Appl. No.: 16/652,725

(22) PCT Filed: Aug. 30, 2018

(86) PCT No.: PCT/MY2018/050057
§ 371 (c)(1),
(2) Date: Apr. 1, 2020

(87) PCT Pub. No.: WO2019/070113
PCT Pub. Date: Apr. 11, 2019

(65) Prior Publication Data
US 2020/0237634 A1 Jul. 30, 2020

(30) Foreign Application Priority Data
Oct. 3, 2017 (MY) ............. PI 2017703730

(51) Int. Cl.
| | |
|---|---|
| *A61K 8/46* | (2006.01) |
| *A61K 8/06* | (2006.01) |
| *A61K 8/20* | (2006.01) |
| *A61K 8/44* | (2006.01) |
| *A61K 8/73* | (2006.01) |
| *A61K 8/891* | (2006.01) |
| *A61K 8/92* | (2006.01) |
| *A61Q 5/02* | (2006.01) |
| *A61Q 5/12* | (2006.01) |

(52) U.S. Cl.
CPC ............. *A61K 8/466* (2013.01); *A61K 8/062* (2013.01); *A61K 8/20* (2013.01); *A61K 8/442* (2013.01); *A61K 8/737* (2013.01); *A61K 8/891* (2013.01); *A61K 8/922* (2013.01); *A61Q 5/02* (2013.01); *A61Q 5/12* (2013.01); *A61K 2800/5426* (2013.01); *A61K 2800/596* (2013.01)

(58) Field of Classification Search
CPC ... A61K 8/466; A61K 2800/5426; A61Q 5/02
See application file for complete search history.

(56) References Cited

U.S. PATENT DOCUMENTS

| | | | | |
|---|---|---|---|---|
| 3,326,808 | A | | 6/1967 | Noseworthy |
| 5,580,494 | A | * | 12/1996 | Sandhu ............... A61K 8/31 510/125 |
| 2008/0009430 | A1 | * | 1/2008 | Hecht .................. C11D 1/37 510/352 |
| 2011/0092405 | A1 | * | 4/2011 | Ryklin ................ A61K 8/375 510/123 |
| 2012/0208898 | A1 | * | 8/2012 | Dong .................. A61K 8/466 514/785 |

FOREIGN PATENT DOCUMENTS

| | | |
|---|---|---|
| CN | 1085248 | 4/1994 |
| CN | 105647665 | 6/2016 |
| FR | 1456758 | 7/1966 |
| WO | 2016/207084 | 12/2016 |
| WO | 2017/019864 | 2/2017 |

OTHER PUBLICATIONS

International Search Report for PCT/MY2018/050057 dated Nov. 27, 2018, 3 pages.
Written Opinion of the ISA for PCT/MY2018/050057 dated Nov. 27, 2018, 5 pages.

* cited by examiner

*Primary Examiner* — Robert A Wax
*Assistant Examiner* — William Craigo
(74) *Attorney, Agent, or Firm* — Nixon & Vanderhye P.C.

(57) ABSTRACT

The invention relates to a shampoo composition for enhancing deposition of oil drop onto a substrate, comprising a mixture of sulfonated methyl ester compounds containing two or more sulfonated methyl esters of a fatty acid having a chain length of 12 to 20 carbon atoms (C12-C20); a zwitterionic surfactant; an oil phase; and a cationic polymer. The shampoo composition may further comprise an inorganic electrolyte such as sodium chloride. The invention also relates to use of the shampoo composition for enhancing deposition of oil drop onto a substrate, wherein the composition comprises a specific blend of sulfonated methyl ester compounds.

17 Claims, 4 Drawing Sheets

| System | C16-SME | SLES-1EO |
|---|---|---|
| 6 wt% Surfactant + 0.1 wt% Jaguar-C-13-S (Initial solution) | | |
| 1 wt% Surfactant + 0.0165 wt% Jaguar-C-13-S (6 times dilution) | | |
| 0.5 wt% Surfactant + 0.008 wt% Jaguar-C-13-S (12 times dilution) | | |
| 0.25 wt% Surfactant + 0.004 wt% Jaguar-C-13-S (24 times dilution) | | |
| 0.0625 wt% Surfactant + 0.001 wt% Jaguar-C-13-S (96 times dilution) | | |

CONDITIONING SHAMPOO COMPOSITION

This application is the U.S. national phase of International Application No. PCT/MY2018/050057 filed Aug. 30, 2018 which designated the U.S. and claims priority to Malaysian Patent Application No. PI 2017703730 filed Oct. 3, 2017, the entire contents of each of which are hereby incorporated by reference.

FIELD OF INVENTION

The invention relates to a conditioning shampoo or cleansing composition. In more particular, the invention relates to a shampoo or cleansing composition containing naturally-derived sulfonated methyl esters (SMEs) and having an improved conditioning effect. This shampoo composition is suitable for use in cleansing and conditioning hair and skin, particularly hair and scalp.

BACKGROUND OF THE INVENTION

Formulations of hair and skin-care products in the industry generally contain small oil drops which condition the hair and skin. Shampoos, cleansing compositions, body washes and other personal care products contain also anionic surfactants, which adsorb and bring negative surface charge to the oil drops and the substrate, such as hair and scalp. The resulting electrostatic repulsion suppresses the oil drop deposition on the substrate.

To overcome this undesired effect, the respective formulations of personal-care composition, such as shampoo and cleansing composition, are also added with a cationic polymer, which serves as a mediator of the drop-to-substrate adhesion. In the bulk of solution, the surfactant and polymer form joint aggregates, also known as "coacervates". Hence, both surfactants and polymers may adsorb on the surfaces of the oil drops and on the solid substrate. They are also present in the wetting films intervening between the oil drop and the substrate. The surfactant-polymer interactions in the bulk and in the thin liquid films are of primary importance for the oil drop deposition process. At higher concentrations, the surfactant in the personal-care formulations hydrophilizes the cationic polymer and the oil drop. Upon rinsing of the personal-care formulations from the substrate, most of the surfactant would be washed away, except for the relatively more hydrophobic polymer molecules that still adsorb on the oil drop while mediating its adhesion to the substrate. As a result, there would be an occurrence of oil drop deposition or adhesion upon a certain degree of dilution of the surfactant in the personal-care composition.

There are a number of studies in the art relating to determination of the amount of deposited oil by means of spectroscopic methods. These methods characterize the total amount of oil as a final result of the deposition process. They, however, do not give information for the occurrence of the oil drop deposition process, and especially, for the degree of dilution, at which the oil drop deposition begins. As oil drop deposition determines the deposition or adhesion of oil drop as well as the active ingredients carried therein onto the substrate such as hair and scalp, it affects the conditioning effect of the personal-care composition to the substrate. However, the oil drop deposition effects of different surfactants used in the personal-care compositions, such as shampoo or cleansing compositions, have not been investigated in the industry to date from the aspect of their related conditioning effect to the substrate.

There are various types of conditioning shampoo or cleansing composition existing in the art, which utilizes sodium lauryl ether sulfate (SLES) as the main surfactant. For example, a hair conditioning shampoo containing 5% to 50% of anionic surfactant such as SLES is disclosed in International publication no. WO 9308787 A2. The hair conditional shampoo can optionally include a zwitterionic surfactant such as betaines and a cationic polymer in its formulation. The document also discloses the use of intermixing silicone oil as a conditioning agent, in which silicone resin is added to enhance the deposition efficiency of the composition. There is, however, no disclosure in the document on the use of any specific type of anionic surfactant in enhancing deposition of oil drop. The oil drop deposition capability of SLES was also not investigated in any of the prior art.

SME, which is also known as $\alpha$-sulfo fatty acid methyl ester or methyl ester sulfonates (MES), is a type of anionic surfactants that has been increasingly used as detergents or wetting agents in numerous industrial and domestic applications, including personal cleansing liquid, shampoo composition, laundry detergents and dish washing detergents. Being derived from natural, renewable resources, such as palm oil, SMEs are known to be biodegradable, renewable and hence considered as green alternative surfactants. SMEs are however, not commonly used in the industry as a main surfactant in shampoo or cleansing composition for hair and scalp.

In a more recent technology as described in European patent no. EP 0796084 A2, a skin cleansing liquid containing a lathering synthetic surfactant is disclosed. This lathering synthetic surfactant can be an anionic surfactant such as acyl isethionates, acyl sarcosinates, alkylglycerylether sulfonates, acyl lactylate, and others. The document discloses that the cleansing liquid has a specific Lipid Deposition Value (LDV) of 5 to 1000 µg of lipid per sq. cm of skin. It also discloses that the composition requires a stabilizer such as crystalline ethylene glycol fatty acid ester to increase liquid deposition onto skin. SME is merely disclosed as a type of anionic surfactant amongst others that may be used in the skin cleansing liquid. However, there has been no disclosure provided in this document on the use of any specific SME compound or specific mixture of SME in a formulation suitable for conditioning hair and scalp. The specific oil drop deposition effect of surfactant is also not disclosed in this document.

There is clearly no teaching provided in the prior art on a conditioning shampoo or cleansing composition containing specific SME compounds, and the relationship between the conditioning effect and oil drop deposition—in the presence of different type of surfactants. Therefore, a shampoo or cleansing composition with its conditioning effect improved from a novel technical aspect is desirable.

SUMMARY OF INVENTION

One of the objects of the invention is to provide a shampoo or cleansing composition for use in cleansing and conditioning hair and scalp, which is capable of enhancing deposition of oil drop onto the substrate (i.e. hair and scalp), hence rendering an improved conditioning effect.

The invention also aims to provide a shampoo or cleansing composition containing a natural and environmental-friendly anionic surfactant such as SME, which is also able to impart an improved robustness of oil drop deposition onto the substrate, as well as to achieve a broadened range of oil drop adhesion values ($C_{adh}$), so as to give rise to a more effective conditioning composition.

At least one of the proceeding objects is met, in whole or in part, by the invention, in which one of the embodiments of the invention describes a shampoo composition for enhancing deposition of oil drop onto a substrate, comprising a mixture of SME compounds containing two or more SMEs of a fatty acid having a chain length of 12 to 20 carbon atoms (C12-C20); a zwitterionic surfactant; an oil phase; and a cationic polymer.

In accordance with one of the embodiments of the invention, the mixture of SME compounds is a mixture between C12 SME and C18 SME; a mixture between C14 SME and C16 SME; a mixture between C14 SME and C18 SME; or a mixture between C16 SME and C18 SME.

According to another embodiment of the invention, the mixture of SME compounds contains 55% to 95% of C16 SME and 5% to 45% of C18 SME.

In certain embodiments, the composition further comprises an inorganic electrolyte as an enhancer for oil drop deposition. Preferably, the inorganic electrolyte can be sodium chloride (NaCl) or potassium chloride (KCl).

One of the embodiments of the invention discloses that the zwitterionic surfactant is an alkyl betaine. Preferably, the zwitterionic surfactant is cocamidopropyl betaine (CAPB). Whilst, another embodiment of the invention discloses that the cationic polymer is a guar gum.

According to one of the preferred embodiments of the invention, the mixture of SME compounds and the zwitterionic surfactant is present in a combination ratio of 5-7.5:1 by weight. Preferably, the mixture of SME compounds and the zwitterionic surfactant is present in a total amount of 6% to 20% by weight of the composition.

It is also disclosed in one of the embodiments that the oil phase includes silicone oil, mineral oil, vegetable oil, animal oil or an oil-in-water emulsion of the oil thereof.

Use of a shampoo composition for enhancing deposition of oil drop onto a substrate is also disclosed in one of the further embodiments of the invention, wherein the composition comprises a mixture of SME compounds containing two or more SMEs of a fatty acid having a chain length of 12 to 20 carbon atoms (C12-C20); a zwitterionic surfactant; an oil phase; and a cationic polymer. Preferably, the composition comprises a specific blend of SME compounds.

The present preferred embodiments of the invention consist of novel features and a combination of parts hereinafter fully described or illustrated in the accompanying drawings and particularly pointed out in the appended claims; it being understood that various changes in the details may be effected by those skilled in the arts but without departing from the scope of the invention or sacrificing any of the advantages of the invention.

BRIEF DESCRIPTION OF THE DRAWINGS

For the purposes of facilitating an understanding of the invention, there is illustrated in the accompanying drawing the preferred embodiments from an inspection of which when considered in connection with the following description, the invention, its construction and operation and many of its advantages would be readily understood and appreciated.

FIG. 1(a)-(d) shows the consecutive stages of the detachment of initially pressed oil drop in the presence of drop/substrate adhesion, according to one of the embodiments of the invention.

FIG. 2(a)-(d) shows the consecutive stages of the detachment of initially pressed oil drop in the absence of drop/substrate adhesion, according to one of the embodiments of the invention.

DETAILED DESCRIPTION OF THE INVENTION

Hereinafter, the invention shall be described according to the preferred embodiments of the invention and by referring to the accompanying description and drawings. However, it is to be understood that limiting the description to the preferred embodiments of the invention and to the drawings is merely to facilitate discussion of the invention and it is envisioned that those skilled in the art may devise various modifications without departing from the scope of the appended claim.

The invention discloses a personal care composition, namely a shampoo or cleansing composition for enhancing deposition of oil drop onto a substrate such as hair and scalp. The shampoo composition comprises a mixture of SME compounds as the main surfactant. The mixture of SME compounds contains two or more long chain SMEs, for example, SMEs of a fatty acid having a chain length of 12 to 20 carbon atoms (C12-C20). As a conditioning shampoo, the composition also contains a zwitterionic surfactant; an oil phase; and a cationic polymer.

In accordance with one of the embodiments of the invention, the mixture of SME compounds can be a mixture between C12 SME and C18 SME; a mixture between C14 SME and C16 SME; a mixture between C14 SME and C18 SME; or a mixture between C16 SME and C18 SME. For example, the mixture of SME compounds is a blend of C16 SME and C18 SME containing 55% to 95% of C16 SME and 5% to 45% of C18 SME by weight of the SME compounds. In another example, the mixture of SME compounds can be a blend of 60% to 90% of C16 SME and 10% to 40% C18 SME, or a blend of 65% to 85% of C16 SME and 15% to 35% C18 SME. Alternatively, the mixture of SME compounds can also be a blend of 90% to 95% of C16 SME and 5% to 10% C18 SME.

In general, C16 and C18 SME can be derived from a natural source, such as plant oils (vegetable oils) or animal fats, including palm oil. Specifically, C16 SME can be obtained from the palmitic acid; while C18 SME can be obtained from stearic acid of palm oil. Both of these SMEs were obtained via sulfonation of methyl ester. C16 SME and C18 SME, respectively, have the molecular structures as shown in the Formula (I) and Formula (II) below:

One of the embodiments of the invention discloses that the zwitterionic surfactant is alkyl betaine, or betaines, particularly CAPB. Preferably, the total amount of surfactant mixture (i.e. mixture of SME compounds and the zwitterionic surfactant) is present in an amount of 6% to 20% by weight of the composition. For example, the total amount of the mixture of SME compounds (e.g. a blend of C16 and C18 SMEs) and the CAPB can present in an amount of 10% to 15% by weight of the composition. In more particular, the total amount of surfactant mixture can be present in approximately 12% to 13% by weight of the shampoo composition. It should be appreciated in the art that the zwitterionic surfactant may also be described as amphoteric surfactant under certain conditions.

According to one of the preferred embodiments of the invention, the mixture of SME compounds and the zwitterionic surfactant, such as CAPB, should be present in a specific combination ratio, namely 5-7.5:1 by weight. At a lower content of CAPB, oil drop deposition of the composition would be higher, but the foaminess of shampoo would be lessened. On the contrary, at higher content of CAPB, the foaminess would be better while the oil drop deposition of the composition would be reduced. Therefore, it is important that the combination ratio between the mixture of SME compounds and the CAPB could be appropriately adjusted, in order to produce a shampoo composition with comparable foaminess and detergency for washing action, while avoiding suppression of oil drop deposition effect for optimum conditioning performance.

As disclosed in another embodiment of the invention, the shampoo composition contains a cationic polymer which can be a guar gum. In more particular, the guar gum can be guar hydroxypropyltrimonium chloride. It can be commercially obtained under the trade name of Jaguar®, for example Jaguar® C-13-S, Jaguar® C-14-S, Jaguar® C-17, Jaguar® Excel, or other cationic polymers of similar chemical composition. The polymer should be larger and relatively more hydrophobic than the surfactant such that it can adsorb to the oil drop in the shampoo composition irreversibly, and would not be rinsed away like the surfactant during the rinsing process of the shampoo composition. The concentration of the cationic polymer can be suitably adjusted by a person skilled in the art to be used in a shampoo composition. It can also be adjusted based on the total surfactant concentration of the shampoo composition.

Without wishing to be bound by the theory, it is believed that the oil-drop deposition of the composition is governed by the electrostatic, hydrophobic, and polymer-bridging surface forces. The anionic surfactant (namely, the SME compounds) and the cationic polymer (for example, the guar hydroxypropyltrimonium chloride) will adsorb on the surface of the oil drop. Because the SME-based surfactant hydrophilizes the cationic polymer and the oil drop during higher concentration of shampoo composition, there would be no oil drop deposition observed when the shampoo composition is applied to the substrate for cleansing or washing. Upon dilution (when the shampoo composition is rinsed off), most of the SMEs would be washed away, while the cationic polymers still adsorb onto the oil drop. Such adsorption mediates the adhesion of the oil drop as well as the active ingredients or nutrients carried therein onto the substrate, namely hair and scalp.

The SME compounds play a vital role in stabilizing the dispersed oil drops and polymer aggregates in the formulation. It is believed that there would be oil drop flocculation due to the occurrence of polymer bridging at low surfactant concentrations. As a result, although most of surfactant would be washed away upon rinsing, a part of it still adsorbs on the oil drops and could influence their attachment to the substrate.

In certain embodiments, the shampoo composition may contain an inorganic electrolyte. For example, the inorganic electrolyte can be NaCl, KCl or the like another electrolyte that does not cause precipitation in the formulation. The addition of inorganic electrolyte, such as NaCl, to a concentrated mixed micellar solution of anionic surfactant and CAPB can also lead to increase of its viscosity, i.e. NaCl can be used as thickener for the shampoo composition.

In the present invention, NaCl can be added to the shampoo composition of the invention, as an enhancer for oil drop deposition. Based on the experimental data, the SME-containing shampoo composition can give rise to a strong oil drop deposition effect, in which its oil drop adhesion value ($C_{adh}$) can be of 0.01% wt to 1.00% wt, especially with the addition of NaCl. Without addition of NaCl, SME-based shampoo composition still imparts a better or enhanced oil drop deposition effect and higher $C_{adh}$ values than shampoo compositions containing other types of main surfactant, for example, SLES. Without wishing to be bound by the theory, it is believed that the increased oil drop adhesion in the presence of NaCl is caused by the enhancement effect of the salt in the segment-segment attraction of the hydrocarbon chains in water, due to the salting out effect as well as the screening of the electrostatic double-layer repulsion. Further, other inorganic electrolytes which may suppress the electrostatic repulsion between the drop and the substrate could also produce an effect similar to that of NaCl.

As disclosed in another embodiment of the invention, the oil phase of the shampoo composition includes silicone oil, mineral oil, vegetable oil, animal oil, or an oil-in-water emulsion thereof, such as oil-in-water emulsion containing silicone oil, mineral oil, vegetable oil or animal oil. The oil used should not be solubilized in the surfactant micelles of the hydrocarbon chain surfactants that are present in the shampoo formulation as well as not be washed out with the surfactant solution during rinsing. Further, the oil used should be less easily oxidized. Preferably, silicone oil is used in the shampoo composition.

In certain embodiments, the shampoo composition may contain active ingredients beneficial to the hair and scalp. Such active ingredients may be solubilized and carried by the oil drop, by the surfactant and other carriers. The active ingredients may be a nutritious component, such as vitamins and minerals, naturally derived plant oils including essential oils, bioflavonoids and anti-oxidants. For example, the vitamins and minerals can be vitamin E (tocotrienols, tocopherols or the combination thereof), vitamin A, silica, magnesium, calcium, potassium, zinc, copper, selenium, chromium and sulfur. The naturally derived plant oils can be argon oil, mint leave oil, marula oil, olive oil, tea tree oil, coconut sheer oil, rapeseed oil, or others.

In certain embodiments, the shampoo composition can further comprises an additive providing specific hair-care effects, such as a hair moisturizing or hydrating agent, oil controlling agent, hair fall controlling agent, hair darkening agent, anti-frizz agent, hair relaxing agent, nourishing agent or hair colour protecting agent. Additionally, the shampoo composition can also contain a preservative, a stabilizing agent, fragrance, colouring agent, or a combination of any two or more thereof.

In accordance with a further embodiment of the invention, the composition is free of non-ionic surfactant, such as coco-fatty-acid-monoethanolamide (CMEA). Although CMEA is also known to be a viscosity regulator to a concentrated mixed micellar solution of anionic surfactant and CAPB, the addition of CMEA to the shampoo composition may, however, suppress the oil drop deposition of the composition onto the substrate. Without wishing to be bound by the theory, it is believed that the nonionic surfactant such as CMEA binds to the hydrocarbon chains and renders them more hydrophilic, thus, suppressing the segment-segment hydrophobic attraction and the effect of polymer bridging within the surfactant system of the shampoo composition.

Use of a shampoo composition for enhancing deposition of oil drop onto a substrate is also disclosed in one of the further embodiments of the invention, wherein the composition comprises a mixture of SME compounds containing two or more SMEs of a fatty acid having a chain length of 14 to 20 carbon atoms (C14-C20); a zwitterionic surfactant; and a cationic polymer. Preferably, the composition comprises a specific blend of SME compounds. For example, the specific blend of SME compounds is a mixture of 55% to 95% of C16 SME and 5% to 45% of C18 SME by weight of the SME compounds.

As set forth in the preceding description, the Pressed Drop Method (PDM) can be used for investigation of the oil drop attachment to a solid substrate. This method gives information about the occurrence and mechanism of the oil drop deposition process. An exemplary method of PDM is further detailed in Example 1. Based on the experimental data, the oil drop deposition effects demonstrated by different types of surfactant are varied. In particular, it is shown in the data that $C_{adh}$ is higher in the presence of C14-SME and C16-SME, while it is lower in the presence of SLES, indicating that the oil-drop deposition is easier and enhanced in SME-based composition. The carbon chain length of SME may also affect the oil drop deposition effect of the shampoo. Therefore, it is preferably that a specific blend SME compounds, e.g. a blend of C16 and C18 SMEs, is used in the shampoo composition of the invention.

Upon rinsing of the shampoo composition off the substrate, the surfactant concentration and oil drop concentration decrease in the same proportion. If the oil drop deposition is proportional to the oil drop concentration, the $C_{adh}$ values of the composition are believed to increase approximately 3 to 4 times (300% to 400%) if SLES is replaced with C16-SME, as derived from the experimental data.

Based on the different substrates, namely hydrophobic and hydrophilic substrates used in the experiment, it can be concluded that oil drop adhesion to the hydrophobic glass is easier as compared to hydrophilic glass, which was to be expected. However, by using the SME-based surfactant in the composition, oil drop deposition can be achieved on both types of substrate.

As set forth in the preceding description, the oil drop of the shampoo composition can include different types of oils. The experiment results using oil drops from silicon oil and plant oil such as sunflower seed oil are shown to be producing identical results for the oil drop deposition effect, as shown by their $C_{adh}$-vs.-$X_{CAPB}$ experimental curves. This is because the oil drops, regardless of their origins, are both covered with a dense adsorption layer from surfactant and polymer, so that the substrate interacts with the adsorption layer, rather than with the oil phase itself. In other words, the drop-to-substrate adhesion is governed by attractive forces in the (surfactant and polymer stabilized) aqueous film intervening between the drop and the substrate. Direct contact of the oil with the substrate can take place after the evaporation of water. Based on the experimental data, $C_{adh}$ is shown to be not sensitive or affected to the different types of oils.

Comparative experiment can also be conducted to study the difference between the use of separate silicone oil drops and silicone oil-in-water emulsion. It is shown in an exemplary experimental result that the oil-in-water emulsion can also generate a comparable $C_{adh}$ values, similar to those obtained by separate silicone oil drops.

Figure 4:
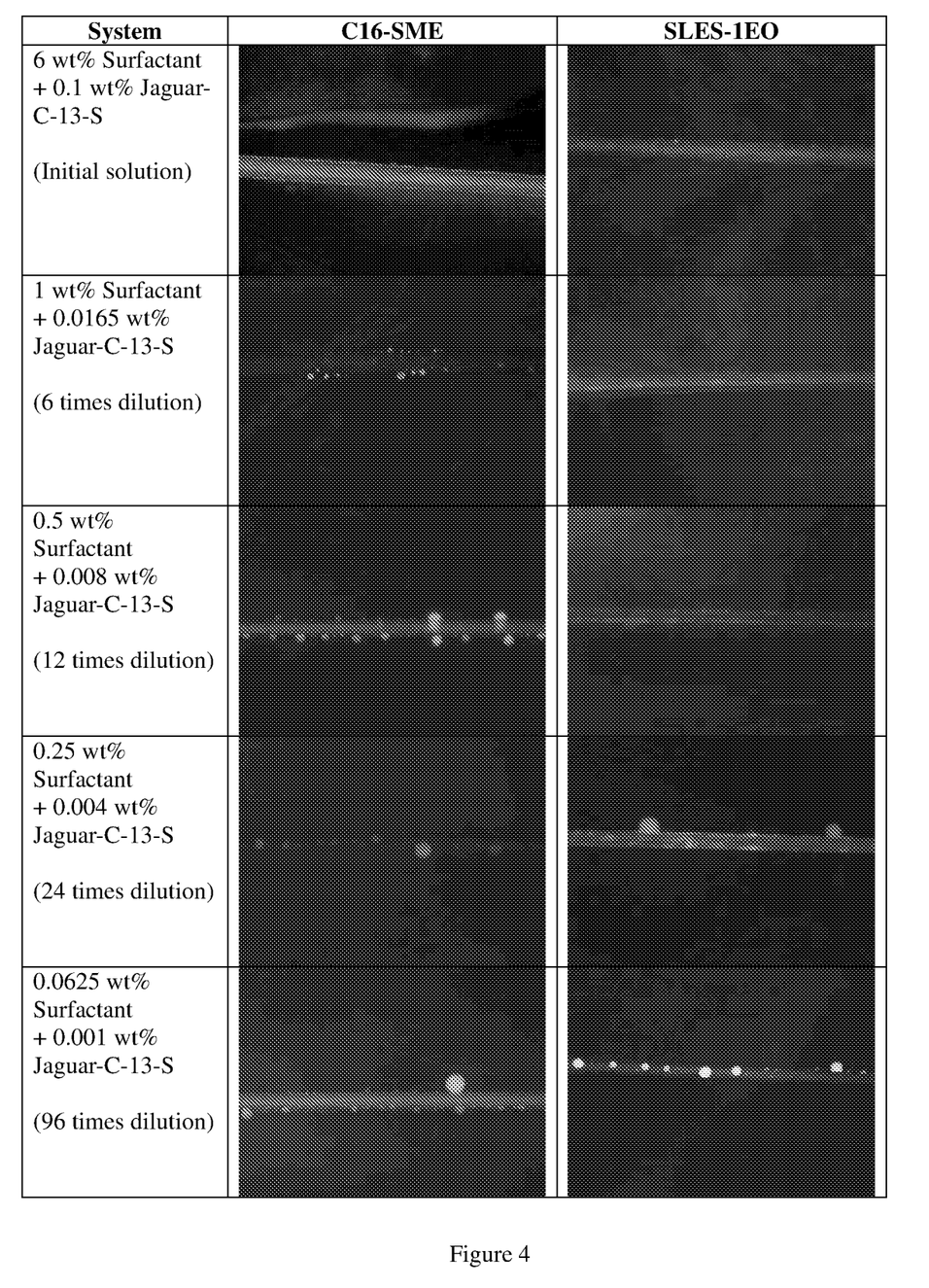
FIG. 4 shows the microscope photographs in reflected light of human hair which is soaked with silicon oil containing the fluorescent dye Bodipy and then immersed in a solution of C16-SME and Jaguar®-C-13-S (left), or SLES-1EO and Jaguar®-C-13-S (right). It is seen that the threshold adhesion concentration is ca. 1 wt % and 0.25 wt % for C16-SME and SLES-1EO, respectively. Different hairs from the same source have been used for different concentrations.

At higher surfactant concentrations, the shampoo composition demonstrates cleaning action, i.e. it has to cause removal (detachment) of oil drops deposited on the substrate as a cleansing composition for substrates such as hair and scalp. As characterized by the enhanced values of $C_{adh}$, the oil drop adhesion of a SME-based shampoo composition occurs at the lower surfactant concentrations, after a certain degree of dilution, rendering a conditioning effect to the hair and scalp. The enhanced oil drop deposition effect can be further shown in the comparative experiments using human hair as substrate, where the utility of SME (instead of SLES) for the enhancement of oil-drop deposition on hair from shampoo formulations can be proven. The utility comparative experiments are further detailed in Example 3, in which the effects of shampoo formulations containing Jaguar C-13-S and C16-SME or SLES-1EO are shown on human hair.

Figure 5:
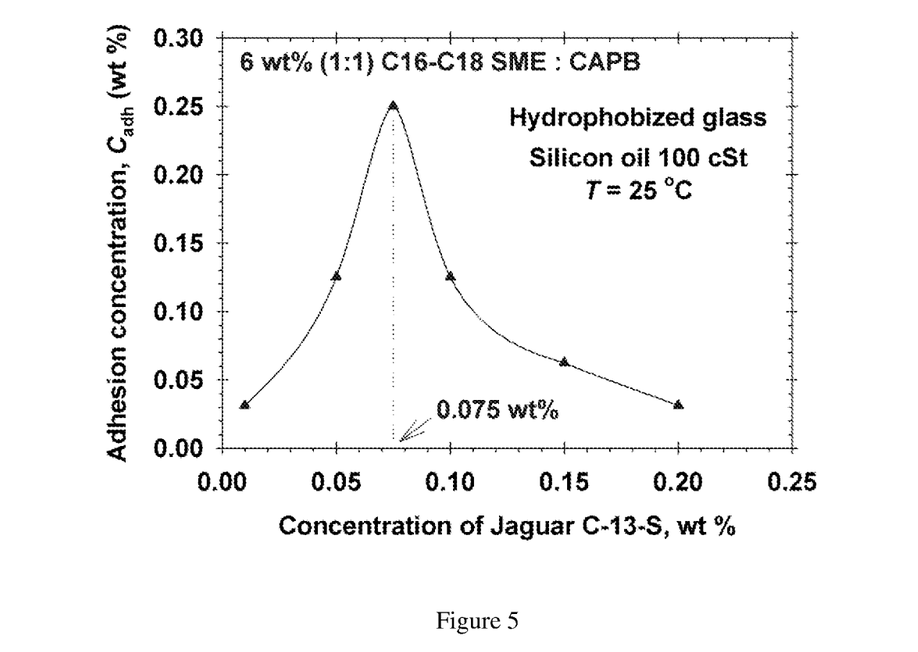
FIG. 5 is a graph showing the adhesion concentration, $C_{adh}$, vs. the concentration of the cationic polymer (Jaguar®-C-13-S), wherein a mixture of SME compounds (C16-C18 SME) is used as the main surfactant, according to one of the embodiments of the invention.

Example 4 shows an experiment on the determination of optimal cationic polymer concentration for oil drop deposition, in which a mixture of SME compounds (C16-C18 SME) is applied as the main surfactant. The concentration of the cationic polymer can be adjusted according to the required properties of the shampoo composition.

EXAMPLE

Example 1 Types of Surfactants Used in the Pressed Drop Method (PDM)

To investigate the effect of surfactant/polymer concentration on the deposition (adhesion) of oil drops on solid substrates in aqueous solutions, a number of surfactants was tested, including different anionic surfactants (C14-SME, C16-SME and SLES); the anionic/zwitterionic surfactant mixture, other surfactants and salt additives.

The SMEs of myristic and palmitic acids (C14 and C16) used in the experiment were obtained from the Malaysian Palm Oil Board (MPOB) and KLK OLEO. C14-SME ($M_w$=344 g/mol) and C16-SME ($M_w$=372 g/mol) were supplied as dry powders. The critical micelle concentrations (CMC) of C14- and C16-SME obtained by electric conductivity measurements are, respectively, 4.0 and 1.1 mM. Whilst, the SLES used has one ethylene-oxide group, and a molecular mass of 332.4 g/mol. It can be commercially obtained from Stepan Co. under the name of STEOL CS-170. The critical micellization concentration of STEOL CS-170 is 0.7 mM determined by both surface tension and conductivity measurements at 25° C. STEOL CS-170 contains alkyl chains in the range of C10-16.

The used zwitterionic surfactant was CAPB, which is a product of Evonik under the commercial name of Tego® Betain F50. It has a molecular mass of 356 g/mol. The CMC of CAPB is 0.09 mM determined by surface tension measurements at 25° C. The cationic polymer was Jaguar® C-13-S, a high molecular weight polymer product of Solvay. The ionic strength was varied by the addition of NaCl, commercially obtained from Sigma, Germany. The aqueous solutions were prepared with deionized water. All experiments were carried out at a temperature of 25° C. The used silicone oil was vinyl terminated polydimethylsiloxane of kinematic viscosity 100 cSt and mass density 0.97 g/cm$^3$ (Gelest Inc.). Sunflower seed oil (SSO) was also used as comparison.

The substrates used in the experiment include hydrophilic microscope slides (glass plates) and hydrophilic microscope slides (which are hydrophilic slides subjected to hydrophobization (silanization) by hexamethyldisilazane (HMDS)).

Example 2 The Pressed Drop Method (PDM)

The PDM experiment was set up based on an experimental model modified from the capillary meniscus dynamometry method as described in the prior art, Danov, et al., 2016. In the experiment, the oil drops were formed at the tip of a metal capillary (hollow needle) of outer diameter 1.83 mm. The metal capillary was mounted in a DSA30 apparatus (Krüss GmbH, Germany) upgraded with a piezo-driven membrane for a precise control of the drop volume. Upon increasing its volume, the drop was pressed against the substrate, which is placed on the bottom of a glass cuvette filled with the investigated aqueous solution. Different degrees of dilution of the initial solution were realized by exchange of portions of the solution with pure water, while the volume of the aqueous phase in the cuvette was kept constant.

Figure 1:
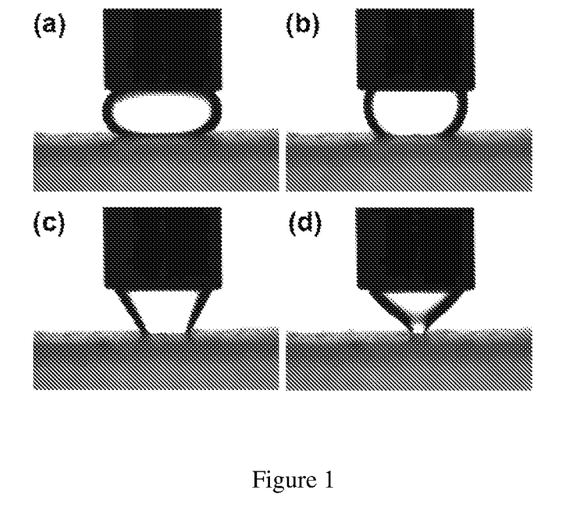
Figure 2:
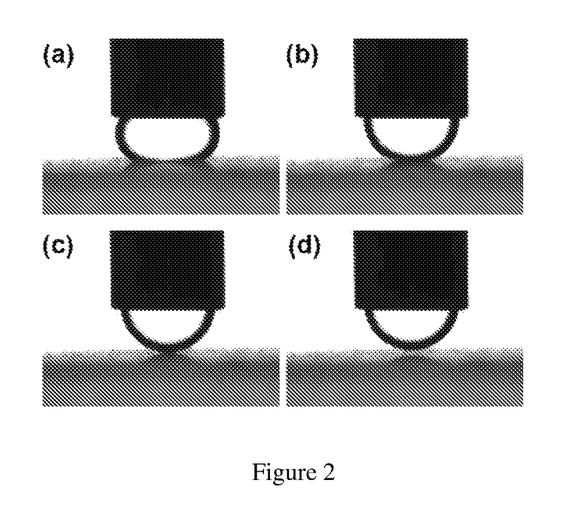

Initially, the cuvette was filled with a concentrated solution of surfactant or surfactant and polymer. The initial total concentration of SLES and CAPB applied was 6 wt % and the initial polymer concentration was 0.1 wt % Jaguar® C-13-S. An oil drop was formed at the tip of a capillary in a polymer and surfactant solution. The drop was first pressed to the substrate and left in contact with the substrate for 10 min, and then detached from it. The drop profile (i.e. the variation of shape of the oil drop) during the detachment indicates whether there was (or there was not) drop adhesion to the substrate. FIGS. 1 and 2 respectively show the consecutive stages of the detachment of initially pressed oil drop in the presence, and absence, of drop/substrate adhesion. The oil drop can be pressed and detached from the substrate several times to check the reproducibility of the experimental result.

The experiment was repeated at different degrees of dilution, which allows one to determine the threshold concentration for drop adhesion, $C_{adh}$. The initial surfactant concentration was relatively high (6 wt %), hence it was decreased in a stepwise manner. At each step, detachment of the drop was carried out to check whether the drop was adherent. At the higher surfactant concentrations the drops were non-adherent, whereas at the lower ones-adherent. The first (highest) surfactant concentration, at which indications for drop adhesion (FIG. 1) were observed, was identified with the threshold concentration for drop adhesion, $C_{adh}$.

To characterize the degree of hydrophilicity/hydrophobicity of the substrate (glass plates), a drop of pure water was placed on its surface and the three-phase contact angle was measured using the devise DSA30 (Krüss GmbH, Germany). The mean contact angles from measurements with many plates are 23.1°±5° for the hydrophilic (non-treated) glass plates and 87.7°±5° for the hydrophobized glass plates. For comparison, the advancing contact angles for hair are between 103° (virgin hair) and 70° (chemically damaged hair), i.e. the contact angle of the hydrophobized plate is in the middle of this interval of angles.

In these experiments, the zwitterionic surfactant was CAPB which was used in mixed solutions with one of the anionic surfactants C14-SME, C16-SME and SLES. The total initial surfactant concentration was fixed to 6 wt %, whereas the weight fraction of CAPB in the surfactant mixture, $X_{CAPB}=w_{CAPB}/(w_{CAPB}+w_{anionic})$. Here, $w_{CAPB}$ and $w_{anionic}$ are the weight concentrations of CAPB and the anionic surfactant, respectively. All solutions contained Jaguar® C-13-S at the same initial concentration of 0.1 wt %.

Figure 3A:
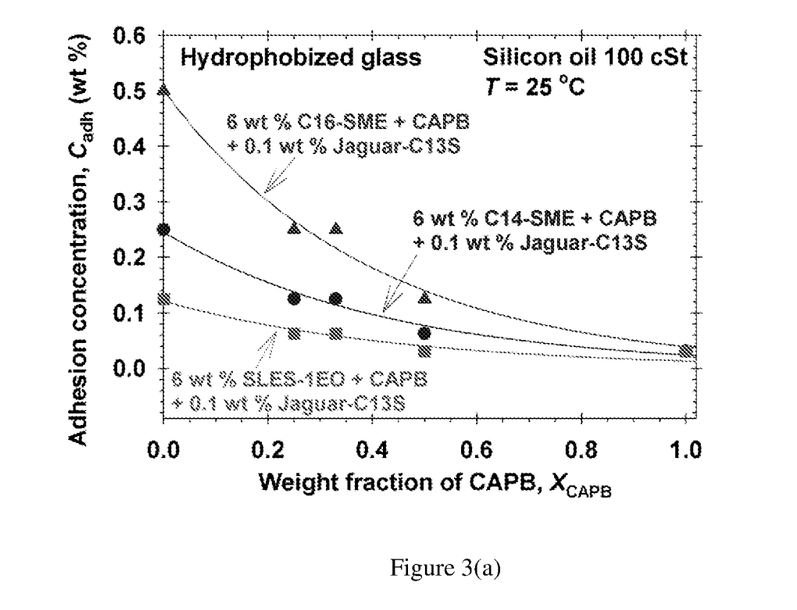
FIGS. 3(a) and (b) are graphs showing the adhesion concentration, $C_{adh}$, vs. the molar fraction of CAPB, $X_{CAPB}$, in mixtures with three different anionic surfactants: SLES-1EO, C14 SME and C16 SME, according to one of the embodiments of the invention, in which (a) is a hydrophobized glass substrate and (b) is a hydrophilic glass substrate. The lines are guides to the eye.

FIG. 3(a) shows a plot of $C_{adh}$ vs. $X_{CAPB}$ for silicon oil and hydrophobized-glass substrate for the three anionic surfactants, C14-SME, C16-SME and SLES. In all cases, the highest $C_{adh}$ (the easiest oil-drop deposition) was observed for 100% anionic surfactant ($X_{CAPB}$=0), whereas $C_{adh}$ is the lowest at 100% CAPB ($X_{CAPB}$=1). $C_{adh}$ monotonically decreases with the rise of $X_{CAPB}$. Moreover, $C_{adh}$ is the highest (the oil-drop deposition is the easiest) in the presence of C16-SME and the lowest in the presence of SLES, the values of $C_{adh}$ for C14-SME being intermediate.

Figure 3B:
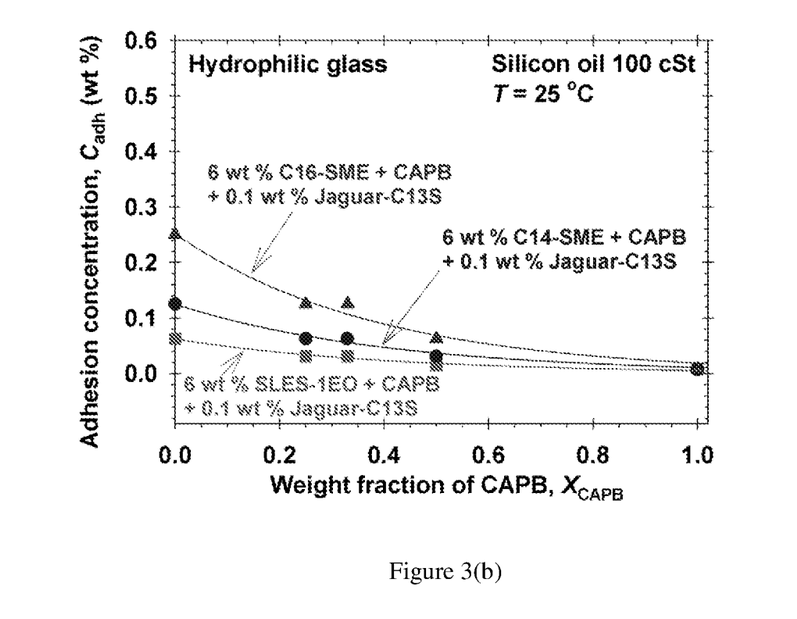

For the hydrophilic-glass substrate as shown in FIG. 3(b), the behavior of the $C_{adh}$-vs.-$X_{CAPB}$ dependences is similar to those for hydrophobized glass as shown in FIG. 3(a), only the values of $C_{adh}$ are about 2 times lower. In other words, the oil-drop adhesion to the hydrophilic glass is more difficult than in the case of hydrophobic glass (θ=23.1), which was to be expected.

The interfacial tensions of the two oils against the surfactant and polymer solutions are not identical. For example, for 6 wt % 3:1 C14-SME:CAPB+0.1 wt % Jaguar® C-13-S the interfacial tension was 3.50 and 2.25 mN/m for the silicon oil and SSO, respectively. In spite of that, the experiments with drops from silicon oil and SSO gave identical results for the $C_{adh}$-vs.-$X_{CAPB}$ experimental curves.

Example 3 Comparative Experiments with Human Hair as Substrate

Comparative experiments were conducted with human hair (as substrate) and shampoo formulations containing Jaguar C-13-S and C16-SME or SLES-1EO, all other conditions being the same as stated in PDM method of Example 2. The silicon oil contains the fluorescent marker (dye) Bodipy (Difluoro{2-[1-(3,5-dimethyl-2H-pyrrol-2-ylidene-N)ethyl]-3,5-dimethyl-1H-pyrrolato-N}boron), Sigma, CAS: 121207-31-6. The hair was first immersed in the silicon oil and, then, in a surfactant and polymer solution at different degrees of dilution.

As demonstrated in FIG. 4, at the higher concentrations, no oil drops remain deposited on the hair, whereas at the lower concentrations many deposited oil drops are observed. The threshold concentration for drop deposition is ca. 4 times higher for C16-SME as compared to SLES-1EO. It is seen that the threshold adhesion concentration is ca. 1 wt % and 0.25 wt % for C16-SME and SLES-1EO, respectively.

Example 4 Optimal Jaguar C-13-S Concentration for Oil-Drop Deposition

By PDM experiments, the threshold adhesion concentration, $C_{adh}$, was measured as a function of the concentration of Jaguar® C-13-S. The obtained dependence (as shown in FIG. 5) exhibits a well pronounced maximum at 0.075 wt % Jaguar C-13-S, which represents the optimal concentration of this cationic polymer for oil-drop deposition at 6 wt % total surfactant concentration (1:1 C16-C18-SME:CAPB). This experiment shows (i) the existence of an optimal ratio of polymer and surfactant and (ii) that the PDM is an appropriate method to determine this optimal ratio.

The invention claimed is:

1. A shampoo composition for enhancing deposition of oil drop onto a substrate, comprising:
   a surfactant mixture consisting of (i) a mixture of sulfonated methyl ester compounds containing two or more sulfonated methyl esters of a fatty acid having a chain length of 12 to 20 carbon atoms (C12-C20); and (ii) a zwitterionic surfactant which is cocamidopropyl betaine;
   an oil phase; and
   a cationic polymer.

2. The shampoo composition according to claim 1, wherein the mixture of sulfonated methyl ester compounds is a mixture between C12 sulfonated methyl ester and C18 sulfonated methyl ester, a mixture between C14 sulfonated methyl ester and C16 sulfonated methyl ester, a mixture between C14 sulfonated methyl ester and C18 sulfonated methyl ester, or a mixture between C16 sulfonated methyl ester and C18 sulfonated methyl ester.

3. The shampoo composition according to claim 1, wherein the mixture of sulfonated methyl ester compounds contains 55% to 95% of C16 sulfonated methyl ester and 5% to 45% of C18 sulfonated methyl ester.

4. The shampoo composition according to claim 1, wherein the composition further comprises an inorganic electrolyte.

5. The shampoo composition according to claim 4, wherein the inorganic electrolyte is sodium chloride or potassium chloride.

6. The shampoo composition according to claim 1, wherein the cationic polymer is a guar gum.

7. The shampoo composition according to claim 1, wherein the mixture of sulfonated methyl ester compounds and the zwitterionic surfactant is present in a combination ratio of 5-7.5:1 by weight.

8. The shampoo composition according to claim 1, wherein the mixture of sulfonated methyl ester compounds and the zwitterionic surfactant is present in a total amount of 6% to 20% by weight of the composition.

9. The shampoo composition according to claim 1, wherein the oil phase is silicone oil, mineral oil, vegetable oil, or an oil-in-water emulsion thereof.

10. The shampoo composition according to claim 1, wherein the surfactant mixture consists of C16 sulfonated methyl ester, C18 sulfonated methyl ester, and cocamidopropyl betaine.

11. The shampoo composition according to claim 10, wherein the cationic polymer is guar hydroxypropyltrimonium chloride.

12. The shampoo composition according to claim 1, which exhibits a higher oil drop adhesion value ($C_{adh}$) compared to a corresponding shampoo composition containing sodium lauryl ether sulfate instead of the mixture of sulfonated methyl ester compounds.

13. A shampoo composition comprising:
   (i) a mixture of anionic surfactants consisting of 55% to 95% of C16 sulfonated methyl ester and 5% to 45% of C18 sulfonated methyl ester by weight;
   (ii) a zwitterionic surfactant comprising cocamidopropyl betaine;
   (iii) an oil phase;
   (iv) a cationic polymer comprising guar hydroxypropyltrimonium chloride; and optionally
   (v) an inorganic electrolyte comprising sodium chloride or potassium chloride;
   wherein the weight ratio of the anionic surfactants to the zwitterionic surfactant is 5-7.5:1 by weight,
   wherein the total amount of the anionic surfactants and zwitterionic surfactant is 6% to 20% by weight of the shampoo composition, and
   wherein the shampoo compositions is free of coco-fatty-acid-monoethanolamide.

14. The shampoo composition according to claim 13, wherein the oil phase is silicone oil, mineral oil, vegetable oil, or an oil-in-water emulsion thereof.

15. The shampoo composition according to claim 13, which exhibits a higher oil drop adhesion value ($C_{adh}$) compared to a corresponding shampoo composition containing sodium lauryl ether sulfate instead of the mixture of anionic surfactants.

16. A shampoo composition comprising:
   (i) a mixture of anionic surfactants consisting of 55% to 95% of C16 sulfonated methyl ester and 5% to 45% of C18 sulfonated methyl ester by weight;
   (ii) cocamidopropyl betaine;
   (iii) silicone oil, mineral oil, vegetable oil, or an oil-in-water emulsion thereof; and
   (iv) guar hydroxypropyltrimonium chloride; and
   (v) sodium chloride or potassium chloride;
   wherein the weight ratio of the anionic surfactants to the cocamidopropyl betaine is 5-7.5:1 by weight,
   wherein the total amount of the anionic surfactants and cocamidopropyl betaine is 6% to 20% by weight of the shampoo composition, and
   wherein the shampoo compositions is free of non-ionic surfactant.

17. The shampoo composition according to claim 16, which exhibits a higher oil drop adhesion value ($C_{adh}$) compared to a corresponding shampoo composition containing sodium lauryl ether sulfate instead of the mixture of anionic surfactants.

* * * * *